US012778514B2

(12) United States Patent
Pahlevan et al.

(10) Patent No.: US 12,778,514 B2
(45) Date of Patent: Nov. 3, 2026

(54) SEQUENTIALLY-REDUCED ARTIFICIAL INTELLIGENCE METHODOLOGY FOR INSTANTANEOUS DETERMINATION OF WAVEFORM INTRINSIC FREQUENCIES

(71) Applicant: University of Southern California, Los Angeles, CA (US)

(72) Inventors: Niema Mohammed Pahlevan, Los Angeles, CA (US); Rashid Alavi Dehkordi, Los Angeles, CA (US); Qian Wang, Lausanne (CH); Hossein Gorji, Zürich (CH)

(73) Assignees: UNIVERSITY OF SOUTHERN CALIFORNIA, Los Angeles, CA (US); ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 703 days.

(21) Appl. No.: 17/987,373

(22) Filed: Nov. 15, 2022

(65) Prior Publication Data

US 2023/0148969 A1 May 18, 2023

Related U.S. Application Data

(60) Provisional application No. 63/280,008, filed on Nov. 16, 2021.

(51) Int. Cl.
*A61B 5/00* (2006.01)
*A61B 5/0205* (2006.01)
(Continued)

(52) U.S. Cl.
CPC .......... *A61B 5/7264* (2013.01); *A61B 5/0205* (2013.01); *A61B 5/0245* (2013.01);
(Continued)

(58) Field of Classification Search
CPC ................ A61B 5/7264; A61B 5/0205; A61B 5/0245; A61B 5/026; A61B 5/14551;
(Continued)

(56) References Cited

U.S. PATENT DOCUMENTS 11,351,382 B2 * 6/2022 Gunderson ........... A61B 5/1116
11,355,244 B2 * 6/2022 Haddad .............. A61N 1/36507
(Continued)

FOREIGN PATENT DOCUMENTS

WO WO-9957647 A1 * 11/1999 ............. A61B 5/411
WO WO-2013096885 A1 * 6/2013 ........... A61B 5/7282
(Continued)

OTHER PUBLICATIONS

Pahlevan et al., "Noninvasive iPhone Measurement of Left Ventricular Ejection Fraction Using Intrinsic Frequency Methodology", Critical Care Medicine, Jul. 2017, pp. 1115-1120, vol. 45(7).
(Continued)

*Primary Examiner* — Jeffrey G. Hoekstra
(74) *Attorney, Agent, or Firm* — Pillsbury Winthrop Shaw Pittman LLP

(57) ABSTRACT

Artificial intelligence (AI) based methodology for instantaneous signal analysis of cardiovascular waveforms using a single or multiple hemodynamic waveform(s) is described. For example, a system comprising at least one programmable processor and a non-transitory machine-readable medium storing instructions which, when executed by the at least one programmable processor, cause the at least one programmable processor to perform operations comprising receiving patient data having one or more cardiovascular waveforms related to a cardiac cycle or a vasculature of a patient; calculating, from the one or more waveforms, at least one output from a signal analysis method, inputting, into a trained artificial intelligence model, cardiovascular
(Continued)

waveforms; determining, utilizing the trained artificial intelligence model, the clinically relevant parameters from a signal analysis method; and in response to determining the output parameters, providing the information about the underlying pathology to a user.

16 Claims, 9 Drawing Sheets

(51) Int. Cl.

| | |
|---|---|
| ***A61B 5/0245*** | (2006.01) |
| ***A61B 5/026*** | (2006.01) |
| ***A61B 5/1455*** | (2006.01) |

(52) U.S. Cl.
CPC .......... *A61B 5/026* (2013.01); *A61B 5/14551* (2013.01); *A61B 5/7257* (2013.01); *A61B 5/7267* (2013.01); *A61B 5/7275* (2013.01)

(58) Field of Classification Search
CPC ................ A61B 5/7257; A61B 5/7267; A61B 5/7275; A61B 5/02108; A61B 5/0022; A61B 5/02416; A61B 5/681; A61B 5/6898; A61B 5/02007
See application file for complete search history.

(56) References Cited

U.S. PATENT DOCUMENTS

| | | | | |
|---|---|---|---|---|
| 11,443,852 | B2 * | 9/2022 | Chakravarthy | A61B 5/7267 |
| 11,617,533 | B2 * | 4/2023 | Pedalty | A61B 5/361 600/518 |
| 11,696,718 | B2 * | 7/2023 | Chakravarthy | G16H 50/70 600/515 |
| 12,053,287 | B2 * | 8/2024 | Attia | G16H 20/10 |
| 2017/0258343 | A1 * | 9/2017 | Pahlevan | A61B 5/0004 |
| 2018/0203978 | A1 * | 7/2018 | Basu | G16H 50/30 |
| 2019/0328243 | A1 * | 10/2019 | Nemati | A61B 5/318 |
| 2020/0108260 | A1 * | 4/2020 | Haddad | A61B 5/7264 |
| 2023/0148969 | A1 * | 5/2023 | Pahlevan | A61B 5/0245 600/324 |

FOREIGN PATENT DOCUMENTS

| | | | | |
|---|---|---|---|---|
| WO | WO-2019028196 A1 * | 2/2019 | A61B 5/4343 |
| WO | WO-2021046237 A1 * | 3/2021 | A61B 7/003 |
| WO | 2022084925 A1 | 4/2022 | |
| WO | WO-2022084923 A1 * | 4/2022 | A61B 5/363 |

OTHER PUBLICATIONS

Pahlevan et al., "Cardiac Triangle Mapping: A New Systems Approach for Noninvasive Evaluation of Left Ventricular End Diastolic Pressure", Fluids, 2019, pp. 1-13, vol. 4(16).

* cited by examiner

SEQUENTIALLY-REDUCED ARTIFICIAL INTELLIGENCE METHODOLOGY FOR INSTANTANEOUS DETERMINATION OF WAVEFORM INTRINSIC FREQUENCIES

CROSS REFERENCE TO RELATED PATENT APPLICATION

This patent application claims the benefit of Provisional Patent Application No. 63/280,008 filed on Nov. 16, 2021, entitled "SEQUENTIALLY-REDUCED ARTIFICIAL INTELLIGENCE METHODOLOGY FOR INSTANTANEOUS DETERMINATION OF WAVEFORM INTRINSIC FREQUENCIES", naming Rashid ALAVI, Qian WANG, Hossein GORJI, and Niema PAHLEVAN as inventors. The entire content of the foregoing patent application is incorporated herein by reference, including all text, tables and drawings.

BACKGROUND

1. Field

The present disclosure relates generally to artificial intelligence (AI) based methodology for instantaneous signal analysis of cardiovascular waveforms using a single or multiple hemodynamic waveform(s).

2. Description of the Related Art

General-purpose function approximators that use Machine Learning (ML) offer new perspectives in the cardiovascular research. Their accuracy, robustness, and universality make them appropriate building blocks for remote health monitoring and early diagnosis. The possibility to develop ML algorithms which could assist diagnosing diseases, has led to a quest for reliable yet efficient classification models of cardiovascular waveforms.

SUMMARY

The following is a non-exhaustive listing of some aspects of the present techniques. These and other aspects are described in the following disclosure.

Some aspects include a system comprising at least one programmable processor; and a non-transitory machine-readable medium storing instructions which, when executed by the at least one programmable processor, cause the at least one programmable processor to perform operations. The operations comprise receiving patient data having one or more cardiovascular waveforms related to a vasculature of a patient; calculating, from the one or more waveforms, at least one output from a signal analysis method, inputting, into a trained artificial intelligence (AI) model, the one or more cardiovascular waveforms; determining, utilizing the trained artificial intelligence model, clinically relevant output parameters for the signal analysis method; and in response to determining the output parameters, providing information about an underlying pathology to a user.

In some embodiments, the one or more waveforms are from a pulse pressure measurement or a pulse oximeter measurement.

In some embodiments, the operations further comprise calculating, from the one or more waveforms, a first intrinsic frequency and a first intrinsic phase associated with the cardiac cycle; and calculating, from the one or more waveforms, a second intrinsic frequency and a second intrinsic phase associated with the vasculature, wherein the clinically relevant output parameters comprise the first intrinsic frequency, the first intrinsic phase, the second intrinsic frequency, and the second intrinsic phase.

In some embodiments, the operations further comprise calculating, from the one or more waveforms, a diastolic intrinsic envelope, and a systolic intrinsic envelope, and relative height of the dicrotic notch (RHDN). The calculating of the first intrinsic frequency, the first intrinsic phase, the second intrinsic frequency, and the second intrinsic phase comprises minimization of a function of the calculated frequencies, phases, and envelopes.

In some embodiments, the operations further comprise training the trained AI model to compute the clinically relevant output parameters by at least inputting training data comprising first intrinsic phase training data. The training data is from a subject that had a specific cardiovascular disease prior to collecting of the training data.

In some embodiments, the operations further comprise obtaining a pulse pressure waveform measurement. The calculating of the at least one output from the signal analysis method is based on the pulse pressure waveform measurement which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, or a pulse-ox waveform.

In some embodiments, the calculating of the at least one output from the signal analysis method is based on a measurement of blood flow.

In some embodiments, the system comprises a client device having a diagnosis module that includes the trained AI model and provides the information about the underlying pathology to a user as a determination of a specific cardiovascular disease. In some embodiments, the client device is a smartphone.

In some embodiments, the operations further comprise calculating, from the one or more waveforms, a Fourier transform harmonic information truncated by any number of frequency of any cardiovascular waveform.

In some embodiments, the operations further comprise calculating, from the one or more waveforms, a basis function expansion extracted from a cardiovascular waveform.

Some aspects include a non-transitory, machine-readable medium storing instructions which, when executed by at least one programmable processor, cause the at least one programmable processor to perform operations comprising: receiving patient data having one or more waveforms related to a cardiac cycle or a vasculature of a patient; calculating, from the one or more waveforms, at least one clinically relevant parameter from a signal analysis method; inputting, into a trained artificial intelligence (AI) model, the one or more waveforms; determining, utilizing the trained AI model, a physiological parameter; and in response to determining the physiological parameter, providing an indication of a cardiac risk to the patient.

In some embodiments, the one or more waveforms are from a pulse pressure measurement or a pulse oximeter measurement.

In some embodiments, the operations further comprise calculating, from the one or more waveforms, a first intrinsic frequency and a first intrinsic phase associated with the cardiac cycle; and calculating, from the one or more waveforms, a second intrinsic frequency and a second intrinsic phase associated with the vasculature. The physiological parameter comprises myocardial parameters, and the myocardial parameters comprise the first intrinsic frequency, the first intrinsic phase, the second intrinsic frequency, and the second intrinsic phase.

In some embodiments, the operations further comprise calculating, from the one or more waveforms, a diastolic intrinsic envelope, and a systolic intrinsic envelope. The calculating of the first intrinsic frequency, the first intrinsic phase, the second intrinsic frequency, and the second intrinsic phase comprises minimization of a function of calculated frequencies, phases, and envelopes.

In some embodiments, the AI model comprises a neural network. The operations further comprise training the neural network to detect signal analysis outputs or clinical or physiological indices directly by at least inputting training data comprising first intrinsic phase training data, wherein the training data is from a patient with a specific cardiovascular disease which is a target for diagnosis.

In some embodiments, the operations further comprise: obtaining a pulse pressure waveform measurement. The calculating of the clinically relevant or physiological parameters are based on the pulse pressure waveform measurement, which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, pulmonary vessel wall waveform, pulmonary pressure waveform, or a pulse-ox waveform.

In some embodiments, the calculating of the clinically relevant or physiological parameters is based on a measurement of blood flow.

In some embodiments, the medium and the processor reside on a client device having a diagnosis module that includes the trained AI model and provides the indication of the cardiac risk to the patient for a cardiovascular disease. In some embodiments, the client device is a smartphone.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
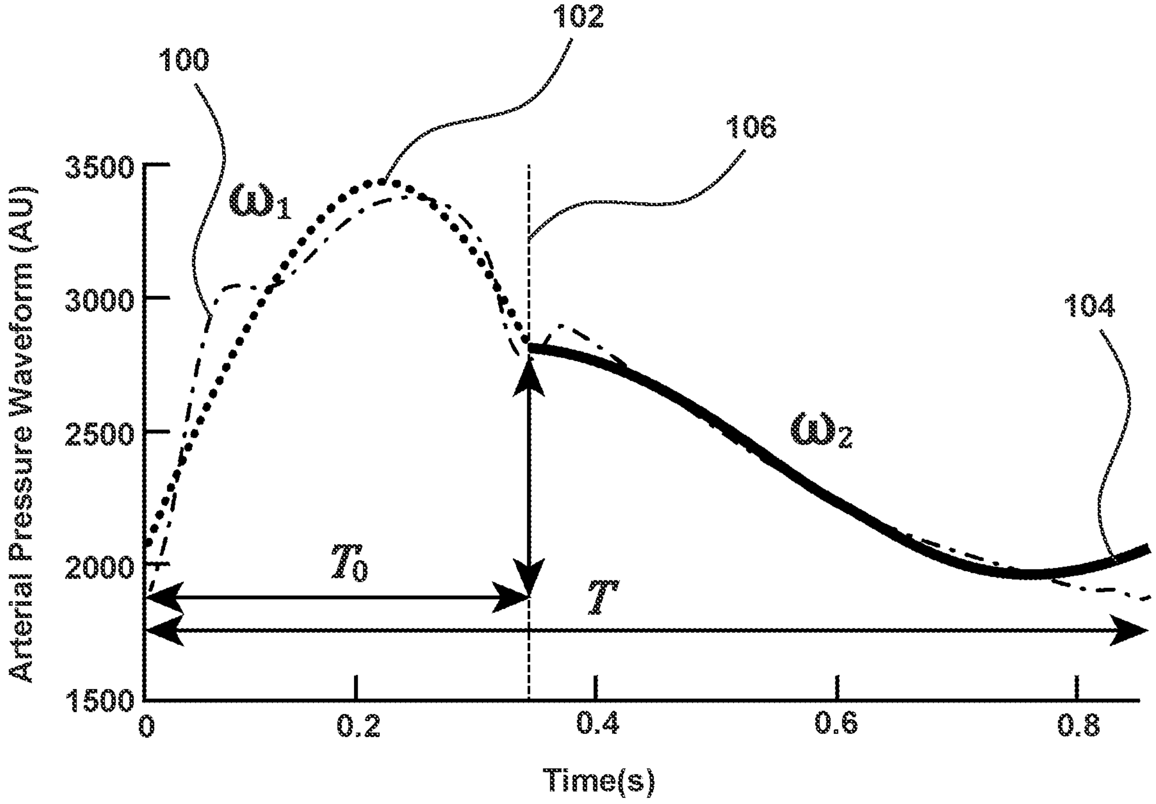
FIG. 1 shows how accurately an intrinsic frequency (IF) reconstructed waveform represents an original waveform, in accordance with various embodiments.

While the invention is susceptible to various modifications and alternative forms, specific embodiments thereof are shown by way of example in the drawings and will be described in detail below. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of sequentially-reduced artificial intelligence (AI) methodology for instantaneous determination of waveform intrinsic frequencies. The inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Some embodiments relate to an AI-based methodology for instantaneous signal analysis of cardiovascular waveforms using a single or multiple hemodynamic waveform(s). The AI-based methodology may map cardiovascular waveforms to a signal analysis output of intrinsic frequency (IF) methodology, thereby avoiding the computationally expensive non-convex L2 minimization problem of the IF methodology. The IF methodology is described in greater detail within "Noninvasive iPhone Measurement of Left Ventricular Ejection Fraction Using Intrinsic Frequency Methodology," Pahlevan et al., Critical Care Medicine, 2017; 45:1115-1120, the contents of which are hereby incorporated by reference in its entirety.

Methods for signal analysis of cardiovascular waveforms such as IF methodology (for arterial waveforms) can provide valuable clinical information about underlying pathology in a patient. Clinical usefulness of the intrinsic frequency methodology for cardiovascular diseases is well-established. Some embodiments include an AI-based methodology for determining intrinsic frequencies using a single or multiple hemodynamic waveform(s). Some embodiments include a procedure for training/testing a machine learning model that can robustly determine waveform characteristics. Additionally, the AI-based methodology described herein can be implemented on a client device, (e.g., a smart phone, a wearable device, a smart ring, etc.). Because the AI-based methodology can be implemented on a client device, the techniques described herein can be used for noninvasive instantaneous applications in clinics or at home. As detailed in International Application Nos. PCT/IB2021/059733 and PCT/IB2021/059735, titled "Noninvasive Cardiovascular Event Detection" and "Noninvasive Infarct Size Determination," respectively, each of which were filed on Oct. 21, 2021, the disclosures of both are hereby incorporated by reference in their entireties, carotid waveforms may be captured using non-invasive techniques and the resulting pressure waves may be analyzed in a machine learning (ML) setting.

Intrinsic Frequency Method

The intrinsic frequency (IF) method is based on a modified version of the sparse time-frequency representation (STFR) method. The IF method extracts the dominant operating frequencies of a waveform. When applied to an arterial blood pressure waveform (the output of the coupled LV-arterial system) (LV is left ventricle), the two dominant frequencies are defined as the first and second intrinsic frequencies ($\omega_1$, $\omega_2$), and relate to the systolic and diastolic phase of the cardiovascular system respectively. In the coupled LV-aorta system, the average angular velocity of rotation (average instantaneous frequency) is defined as oi, while the average angular velocity during diastole is defined as $\omega_2$. It has been shown that the LV contractility and afterload can be represented as functions of $\omega_1$ and $\omega_2$. It should be noted that the IF frequencies are fundamentally different than Fourier harmonics or any other resonance-type frequencies. The IF methodology only requires a single pressure waveform, with the main advantage of working with the waveform morphology alone. Therefore, there is no need to calibrate the pressure data, and the IF parameters can be acquired noninvasively, instantaneously, and inexpensively as simple as using a smartphone, arterial applanation tonometry, etc. From a mathematical point of view, the IF method solves a nonlinear optimization problem for a cardiac cycle to minimize the following objective function:

$$\|p(t) - \chi(0, T_0)[a_1\cos(\omega_1 t) + b_1\sin(\omega_1 t)] - \chi(T_0, T)[a_2\cos(\omega_2 t) + b_2\sin(\omega_2 t)] - c\|_2^2 \qquad \text{Equation (Eq) 1}$$

subject to:

$$a_1\cos(\omega_1 T_0) + b_1\sin(\omega_1 T_0) = a_2\cos(\omega_2 T_0) + b_2\sin(\omega_2 T_0) \text{ and} \qquad \text{Eq. 2a}$$

$$a_1 = a_2\cos(\omega_2 T) + b_2\sin(\omega_2 T), \qquad \text{Eq. 2b}$$

where a, b, and c are the constants. T0 is the dicrotic notch time (corresponding to time of decoupling of LV and aorta), and T is the cardiac cycle period.

The $L_2$ minimization problem of Equation 1 is subject to two nonlinear constraints including the continuity constraint at $T_0$ and the periodicity constraint of the waveform (Eqs. 2a, 2b). In Equation 1, $\chi(a, b)$ denotes the indicator function in which $\chi(a, b)=1$ if $a \le t \le b$, and $\chi(a, b)=0$ otherwise; and p(t) refers to the arterial pressure waveform (e.g., ascending aorta, carotid, radial pressure waveform). After solving the defined non-convex minimization problem for seven optimization variables [$a_1$, $b_1$, $\omega_1$, $a_2$, $b_2$, $\omega_2$, c], the optimum value of the IF parameters may be obtained. The IF parameters may be used to systematically reconstruct the arterial pressure by a good agreement.

FIG. 1 shows how accurately an IF-reconstructed waveform represents an original waveform. FIG. 1 shows an original raw pressure waveform 100 in an arbitrary unit (AU) overlaid on top of a reconstructed waveform 102 and 104, which was reconstructed using the IF method, leading to a five-dimensional space (IF space) with $\omega_1$, $\omega_2$, $T_0$, T, and RHDN (green arrow divided by the total range) as the main dimensions (with the location of the dicrotic notch marked by the vertical dotted line 106).

Figure 2:
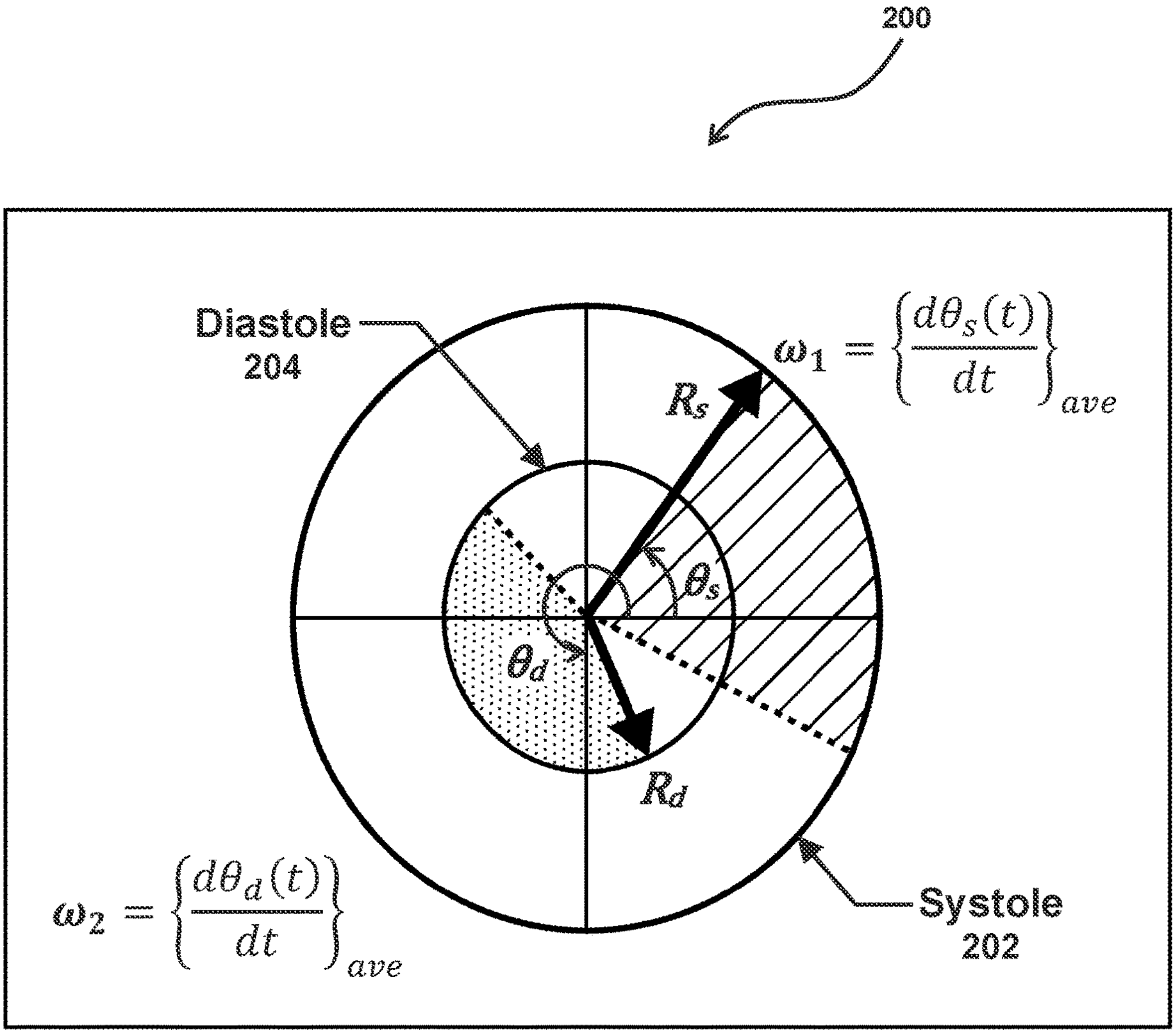
FIG. 2 illustrates a trigonometric circle concept used to define IF parameters such as intrinsic envelope of the systolic phase (Rs), intrinsic envelope of the diastolic phase (Rd), and intrinsic envelope ratio (ER), in accordance with various embodiments.

Using a trigonometric circle concept, as detailed in FIG. 2, other IF parameters such as intrinsic envelope of the systolic phase ($R_s$), intrinsic envelope of the diastolic phase ($R_d$), and intrinsic envelope ratio (ER) can be defined as follows:

$$R_s = \sqrt{a_1^2 + b_1^2},\ R_d = \sqrt{a_2^2 + b_2^2},\ ER = \frac{R_s}{R_d}. \qquad \text{Eq. 3}$$

The ER has been shown to have significant changes over an acute myocardial infarction (MI) (heart attack). Using the intrinsic envelopes and the intrinsic frequencies along with the trigonometric circle concept, the IF method can be visualized differently for both systolic and diastolic phases. For example, FIG. 2 illustrates intrinsic frequency (IF) visualization during systole 202 and diastole 204, through the intrinsic frequencies ($\omega_1$, $\omega_2$) and the intrinsic envelopes ($R_s$, $R_d$) of the systolic and diastolic phases, where $d\theta/dt$ is the instantaneous frequency, and $\theta_s$, $\theta_d$ are the intrinsic phases during systole and diastole, respectively. (Note: in general, $R_s \neq R_d$).

Machine Learning Procedure for Cardiovascular Waveform Intrinsic Frequencies Analysis Considering the two-coupled IF method (two intrinsic frequencies) as an example of a signal analysis method, some embodiments include an AI-based method that may be used to efficiently map waveforms to the intrinsic frequency parameters. Different network architectures can be considered for this task, such as machine learning models including a feedforward neural network (FNN), a recurrent neural network (RNN), and temporal convolutional neural network (TCNN).

Figure 3:
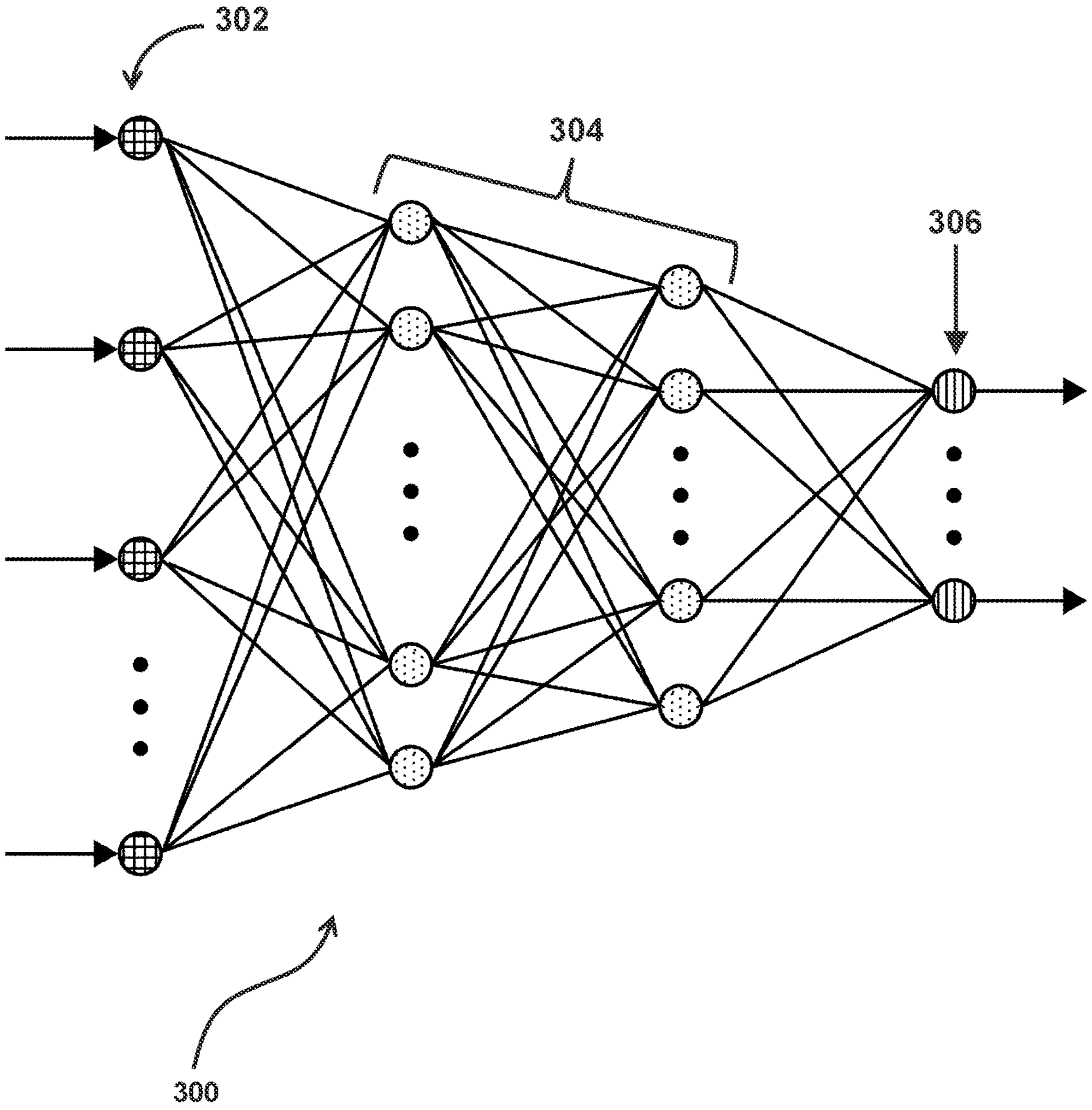
FIG. 3 illustrates a sample feed forward neural network structure comprising an input layer, several hidden layers and an output layer, in accordance with various embodiments.

A sample FNN structure 300 comprising an input layer 302, several hidden layers 304, and an output layer 306 is shown in FIG. 3. However, the machine learning model may be any of the following types of machine learning models: Ordinary Least Squares Regression (OLSR), Linear Regression, Logistic Regression, Stepwise Regression, Multivariate Adaptive Regression Splines (MARS), Locally Estimated Scatterplot Smoothing (LOESS), Instance-based Algorithms, k-Nearest Neighbor (KNN), Learning Vector Quantization (LVQ), Self-Organizing Map (SOM), Locally Weighted Learning (LWL), Regularization Algorithms, Ridge Regression, Least Absolute Shrinkage and Selection Operator (LASSO), Elastic Net, Least-Angle Regression (LARS), Decision Tree Algorithms, Classification and Regression Tree (CART), Iterative Dichotomizer 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Causality Networks (CN), Multinomial Naive Bayes, Averaged One-Dependence Estimators (AODE), Bayesian Belief Network (BBN), Bayesian Network (BN), k-Means, k-Medians, K-cluster, Expectation Maximization (EM), Hierarchical Clustering, Association Rule Learning Algorithms, A-priori algorithm, Eclat algorithm, Artificial Neural Network Algorithms, Perceptron, Back-Propagation, Hopfield Network, Radial Basis Function Network (RBFN), Deep Learning Algorithms, Deep Boltzmann Machine (DBM), Deep Belief Networks (DBN), Convolutional Neural Network (CNN), Deep Metric Learning, Stacked Auto-Encoders, Dimensionality Reduction Algorithms, Principal Component Analysis (PCA), Principal Component Regression (PCR), Partial Least Squares Regression (PLSR), Collaborative Filtering (CF), Latent Affinity Matching (LAM), Cerebri Value Computation (CVC), Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA), Ensemble Algorithms, Boosting, Bootstrapped Aggregation (Bagging), AdaBoost, Stacked Generalization (blending), Gradient Boosting Machines (GBM), Gradient Boosted Regression Trees (GBRT), Random Forest, Computational intelligence (evolutionary algorithms, etc.), Computer Vision (CV), Natural Language Processing (NLP), Recommender Systems, Reinforcement Learning, Graphical Models, or separable convolutions (e.g., depth-separable convolutions, spatial separable convolutions, etc.).

In some embodiments, a signal or waveform may be represented as a high dimensional (n) vector, for example, which can be input to the model. In some embodiments, a high dimension vector comprises a vector with, for example, n greater than 32, n greater than 64, n greater than 128, n greater than 256, n greater than 512, etc. In some embodiments, an output vector from the model is of low dimension (e.g., n is less than 128, n is less than 64, n is less than 32, n is less than 16, n is less than 10, or n is less than 3). Thus the model (e.g., neural network) may have a converging structure. In other words, the number of neurons in each layer may decrease from the input layer to the output layer. Alternatively, one or more layers of the network may have the same number of neurons as a previous layer. Each layer may be a fully or partially connected layer, for example.

AI-Based Method for Determination of Cardiovascular Intrinsic Frequency Parameters In a first step, scaling, normalization, and data resampling techniques may be applied to the waveforms (signals) to reconcile data over different species (different physiological states) and different measurement devices (different sampling rates and measurement units). In a second step, signal analysis output parameters may be computed from the prepared arterial (pressure or diameter) waveform (e.g., using equations (1) to (3) for the IF method). In a third step, a machine learning or artificial intelligence (AI) model (e.g., including a neural network) or any other artificial intelligence method such as machine learning methods comprising input (waveform signal and/or other waveform parameters), hidden (with at least two neurons/nodes), and output layers (with at least one neuron/node revealing signal analysis output parameters) can be selected and used. In a fourth step, the AI model may be fully trained using a training algorithm (e.g., Levenberg-Marquardt algorithm), using a combination of synthetic, preclinical, and clinical data measured by different devices, for example. In a fifth step, the trained machine learning model (e.g., trained AI model) may be (blindly) tested (e.g., machine learning model validation) on additional cases/subjects to ensure the accuracy of the model. In some embodiments, if the accuracy of the model after training is less than a threshold accuracy (e.g., 85% accurate or more, 95% accurate or more, etc.), then the model may be re-trained using the same, updated, or new training data.

As mentioned above, waveforms (signals) including various data (e.g., which may be input to the trained machine learning model) can be easily measured non-invasively and instantaneously using portable devices. For example, a smartphone, a wearable device (e.g., smartwatch, smart bracelet, smart ring, etc.) may be used to capture the data (e.g., blood pressure measurements, ECGs, pulse rate data, etc., LVEDP values, etc.). Outputs of the waveform (signal) analysis can be approximated based on an input carotid pressure waveform, for example. As an alternative to the carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, a pulse-ox waveform, etc., can be used. As another alternative, flow or velocity waveforms can also be used.

Figure 4:
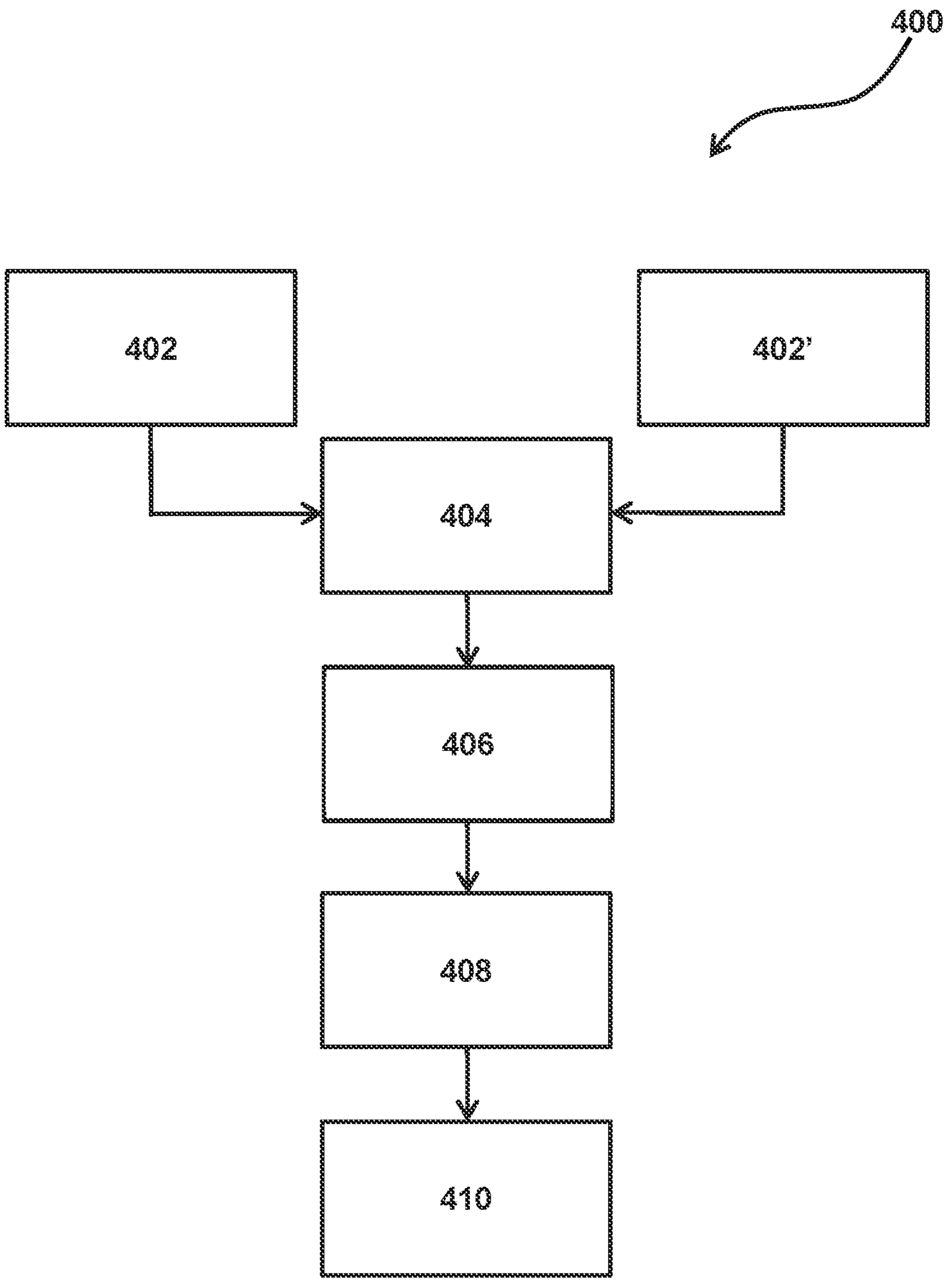
FIG. 4 shows an example block flow diagram for determination of signal analysis outputs according to the operational method steps described herein, in accordance with various embodiments.

FIG. 4 shows an example block flow 400 diagram for determination of signal analysis outputs according to the operational method steps described herein. At steps 402 and 402', patient data having one or more cardiovascular waveforms related to a cardiac cycle or a vasculature of a patient is received. In this example, step 402 comprises receiving pulse pressure/displacement waveform (signal) measurements (e.g., carotid, radial, femoral, etc.). Step 402' comprises receiving a pulse ox waveform (signal) measurement. Step 404 comprises performing the scaling, normalization, and data resampling procedure described above to reconcile data over different species (different physiological states) and different measurement devices (different sampling rates and measurement units). Step 406 comprises calculating, from the one or more waveforms, at least one output from a signal analysis method. In this example, this may include computing exact solutions of the IF method technique described above. Step 408 comprises inputting, into a trained artificial intelligence (AI) model, the one or more cardiovascular waveforms. This may also include training and testing the AI model (which can have many different possible structures as described above). Step 410 comprises determining, utilizing the trained artificial intelligence model, clinically relevant output parameters for the signal analysis method (e.g., determining the IF parameters described above). In some embodiments, step 410 also includes, in response to determining the output parameters, providing information about an underlying pathology to a user.

As detailed in International Application Nos. PCT/IB2021/059733 and PCT/IB2021/059735, titled "Noninvasive Cardiovascular Event Detection" and "Noninvasive Infarct Size Determination," respectively, each of which were filed on Oct. 21, 2021, the disclosures of both are hereby incorporated by reference in their entireties, carotid waveforms may be captured using non-invasive techniques and the resulting pressure waves may be analyzed in an ML setting. In some embodiments, translating the temporal carotid pressure to its frequency domain counterpart may define a regression problem based on the recently introduced Intrinsic Frequencies (IF) methodology, which is described in greater detailed within "Noninvasive iPhone Measurement of Left Ventricular Ejection Fraction Using Intrinsic Frequency Methodology," Pahlevan et al., Critical Care Medicine, 2017; 45:1115-1120, the contents of which are hereby incorporated by reference in their entirety.

To construct (i.e., train, validate, and test) the machine learning or AI model described above, an assortment of various carotid waveform signal sources may be used, including clinical databases (measured by various devices including Tonometry, Vivio, and iPhone) and/or a physiologically generated synthetic database, for example. The synthetic database can ensure the mathematical training of the IF method. The clinical databases can enrich the training algorithm and subsequently the model for subsequent clinical purposes (e.g., preparation for real-world physiological variations and noises, which are not considered by the first intrinsic mode function (IMF) assumption of the IF method). Additionally, a portion of the clinical database may be utilized for a blind-test process, which may be a completely blind-test, to assess the robustness/accuracy of the trained model more deeply.

In some embodiments, one or more pre-processing steps may be performed to the data. In some embodiments, a waveform normalization procedure may be performed. The IF method works with the shape (morphology) of an arterial pressure waveform (or some other waveform). Therefore, any device capable of recording the arterial waveform (e.g. smartphone, arterial applanation tonometry, etc.) with any arbitrary measurement unit is compatible with the IF method. Accordingly, a broad range of values even in different orders of magnitude may be recorded for the same arterial waveform depending on the measurement unit. Although the waveform shape and the IF parameters are not dependent on the unit of the recorded signal, when it comes to collecting, archiving, or analyzing a substantial number of datapoints for the IF method (e.g., machine learning, deep learning, etc.), it is highly effective to reduce the size of the archive without loss of generality. As new devices and techniques are developed for non-invasive waveform measurements, which might lead to different measurement units or ranges of future signal records, the techniques and methodologies described herein may be applied.

As such, some embodiments include a new standard coordinate system for the arterial waveforms through which measurements of different devices (or even different species) can fall within the same range of signals and IF parameters. In addition to the new standard coordinate system, a normalized time may also be proposed along with the new standard coordinate setup. These systems and techniques may generate the same cardiac cycle period (T'=1) for all the arterial waveforms. Such a coordinate system can be achieved for all the arterial waveforms (e.g., coming from different sensor platforms), thereby saving enormous storage and time (especially in the big-data studies).

In some embodiments, a data normalization process (e.g., Step 404 in FIG. 4) may include the following steps, and/or other steps: (1) the minimum value $P_{min}=P(t)$ of the signal or waveform (given in any arbitrary measuring unit) may be subtracted from the measured P(t) at all times of the entire cardiac cycle (i.e., $P(t)-P_{min}$, $0 \le t \le T$); (2) the resulting waveform may be divided by its range over the entire cardiac cycle (i.e., $\hat{P}(t)=(P(t)-P_{min})/(P_{max}-P_{min})$, $0 \le t \le T$)); and/or (3) data may be normalized in time by scaling t with the length T of the entire cardiac cycle (i.e., $\hat{P}(\tau)=\hat{P}(\tau(t))$, $\tau=t/T$, $0 \le \tau \le 1$), where $\tau$ stands for normalized time.

The data produced via the data normalization process may lead to a scaled waveform ($\hat{P}(\tau)$). From here, the IF method may be applied to the scaled waveform, and new (non-dimensional) IF parameters may be extracted as a result. The IF parameters may include a first intrinsic frequency $\omega_1$ of a systolic portion of the cardiac cycle of the patient, a second intrinsic frequency $\omega_1$ of a diastolic portion of the cardiac cycle, a systolic intrinsic phase angle $\varphi_1$, a diastolic intrinsic phase angle $\varphi_2$, a systolic envelope $R_s$, a diastolic envelope $R_d$, an envelope ratio ($R_s/R_d$), a relative height of the dicrotic notch (RHDN), an amount of time between a beginning of the systolic portion of the cardiac cycle and the dicrotic notch, an amount of time between a beginning of the systolic portion and an end of the diastolic portion, a maximum rate of change of a rising portion of the systolic portion of the cardiac cycle, or other parameters.

Using Eqs. 1 to 3 along with the scaling procedure, the non-dimensional IF parameters can be obtained in terms of the original IF parameters as follows:

$$\hat{\omega}_1 = \omega_1 T,\ \hat{\omega}_2 = \omega_2 T,\ \hat{c} = \frac{c - P_{min}}{P_{max} - P_{min}},\ \hat{T}_0 = \frac{T_0}{T}, \quad \text{Eq. 4}$$

$$\hat{R}_s = \frac{R_s}{P_{max} - P_{min}},\ \hat{R}_d = \frac{R_d}{P_{max} - P_{min}},\ \widehat{ER} = \frac{\hat{R}_s}{\hat{R}_d}. \quad \text{Eq. 5}$$

The normalization procedure (e.g., Step 404 in FIG. 4) results in a normalization of the range of waveform values as well as the length of the cardiac cycle. Therefore, the aforementioned process can enable cross-platform comparisons of IF applied to any arterial waveform (measured by an arbitrary sensor platform) regardless of cardiac cycle length and initial measuring units. Additionally, the normalized IF parameters (reduced-order parameters, Eq. 4) corresponding to the scaled carotid artery waveforms, can significantly reduce the size of the data while keeping the physiological meaning of the waveforms.

In some embodiments, a waveform resampling procedure (e.g., a different portion of Step 404 shown in FIG. 4) may be performed. A candidate AI model may be configured to receive the scaled carotid waveform as an input (as well as the dicrotic notch time), and produce the normalized IF parameters as model outputs. The AI model may import the discrete datapoints of a scaled carotid waveform. Different measurement devices may have different sampling rates and, even for a given measurement device, the cardiac cycle period may be different for different individuals, as well as for the same individual. In some embodiments, the normalized carotid waveforms may have different datapoint (vector) sizes. To obtain a globally applicable AI model, a fixed number of datapoints (e.g., N=500) may be used as the waveform size for input into the AI model. In some cases, the input (waveform) vectors are down/over-sampled, which may generate inputs of uniform dimension for the network. The generated inputs may enable usage of any measurement device for capturing pressure waveform measurements. As an example, the waveform down/over-sampling process may be performed using a spline interpolation to space $R^{500}$ (where n=500 is an example of the dimension for the selected space).

Figure 5:
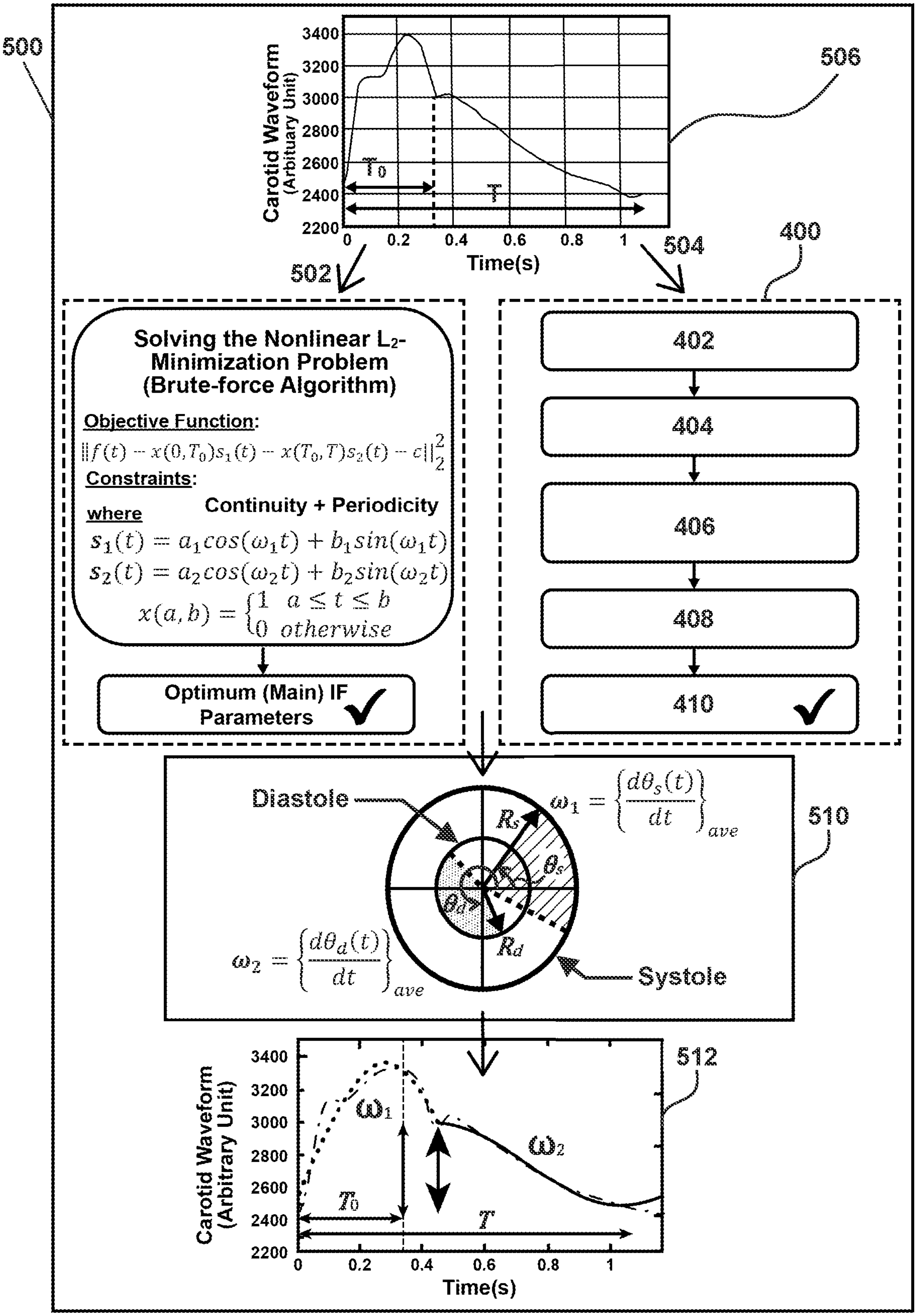
FIG. 5 illustrates a flowchart of a preliminary study comparing optimization based IF parameter determination to AI based IF parameter determination using carotid waveforms, in accordance with various embodiments.

FIG. 5 illustrates a flowchart 500 of a preliminary study comparing optimization based IF parameter determination 502 to AI based IF parameter determination 504 (see flow 400 described above) using carotid waveforms 506. In the study, optimization-based and AI based methods were performed in parallel to determine whether each method output the same or similar results. The outputs from each method were mapped to an intrinsic frequency space 510 and an IF reconstruction of a carotid waveform 512 was performed.

In some embodiments, AI model training may be performed. In some embodiments, input training data may include notch times and interpolated waveforms in space $R^{501}$. Training output may include corresponding IF parameters, including $\omega_1$, $\omega_2$, $R_1$, $\phi_1$, c, and/or other parameters. R1 and $\phi_1$ are the first intrinsic envelope and the first intrinsic phase, respectively. The output (variables) may have different scales. Therefore, for cases where the output variables have different scales, it may be necessary to perform feature scaling (as described above) to train a model that is accurate for all (or substantially all) output variables. In some embodiments, feature scaling for a variable y is defined as:

$$\hat{y} = \frac{y - \text{mean}(y)}{std(y)} \quad \text{Eq. 6}$$

where mean is the average value, and std stands for the standard deviation.

During training, weights and biases of the AI model may be adjusted by minimizing a loss function and/or by other methods. For example, a mean squared error (MSE) may be used as the loss function. In some embodiments, an $L_1$ or $L_2$ regularization may be added to the loss function to avoid over-fitting. An amount of regularization may be controlled using a hyper-parameter λ. The optimal weights and biases may be obtained using the Adam stochastic optimizer, as one example. In each epoch, a training data set may be shuffled and then divided into several mini-batches. The weights and biases may be updated by minimizing the loss function on each mini-batch. In some cases, this updating may occur once. In some embodiments, the training is performed for a sufficient number of epochs to obtain a converged network. The convergence speed of the training can be controlled by the learning rate, (e.g., $10^{-3}$). In some embodiments, an AI model may be trained with one or more (e.g., 10) restarts to avoid the influence of random initialization of weights and biases on the training.

Different quantities of hyper-parameters may be used for the training of the AI model. For example, the number of hidden layers $n_L \in [3,4,5]$; the number of neurons of the first hidden layer $n_N \in [512,256,128]$; the regularization function $f_{reg} \in [L_1, L_2]$; and the regularization coefficient $\lambda \in [10^{-5}, 10^{-6}, 10^{-7}]$. A grid-search of the hyper-parameters may be performed to find the optimal network configuration. The trained AI model that has the smallest validation error may be selected as the final model. Additional analysis (e.g., PCA analysis) may be performed to ensure that the features of the model do not contribute too much to the model result.

As an example, the trained AI model may include four hidden layers with 256, 128, 64, and 32 neurons, may be trained with the $L_2$ regularization, and the coefficient of the regularization may be $10^{-6}$. The training may be performed using the PyTorch machine learning library or other conventional machine learning platforms.

As an example, a test error of the AI model is presented in Table 1.

TABLE 1

| Output | RMSE | Relative error (%) | Max absolute error |
|---|---|---|---|
| $\omega_1$ | 0.769479 | 0.856751 | 5.326436 |
| $\omega_2$ | 1.331688 | 2.183796 | 12.688819 |
| $R_1$ | 0.00619 | 0.85585 | 0.055652 |

TABLE 1-continued

| Output | RMSE | Relative error (%) | Max absolute error |
|---|---|---|---|
| $\phi_1$ | 0.013578 | 4.613535 | 0.1323 |
| c | 0.004977 | 1.499961 | 0.028939 |

Figure 6:
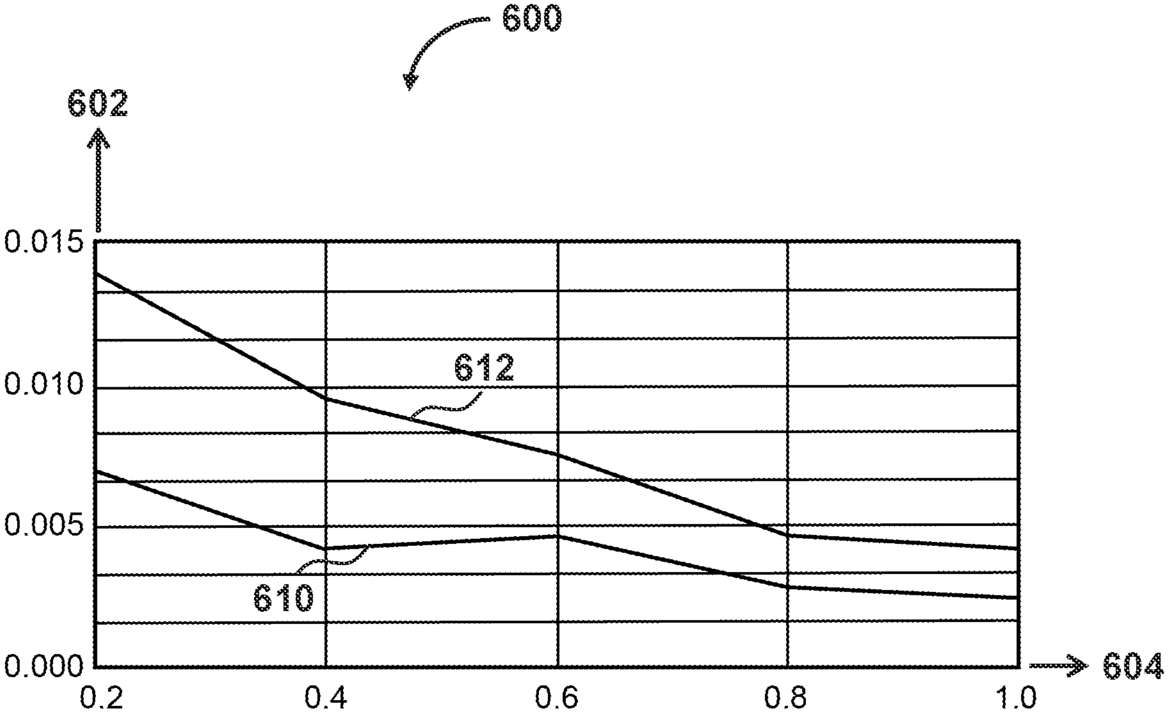
FIG. 6 illustrates a sensitivity of an accuracy of a trained AI model on an amount of training data, in accordance with various embodiments.

RMSE: Root mean square error
Relative error and max absolute error are indicators of the difference between the model outputs and the expected outputs The impact of the amount of training data on the accuracy of the AI model was investigated by training AI models with different amounts of training data. FIG. 6 provides a chart 600 that illustrates the sensitivity 602 of the accuracy the trained AI model to the amount 604 of training data. FIG. 6 illustrates a training loss 610 and a validation loss 612 (Training loss and validation loss were calculated using the training and validation data, respectively.) As shown in FIG. 6, the sensitivity 602 of the accuracy the trained AI model decreases as the amount 604 of training data increases.

Figure 7:
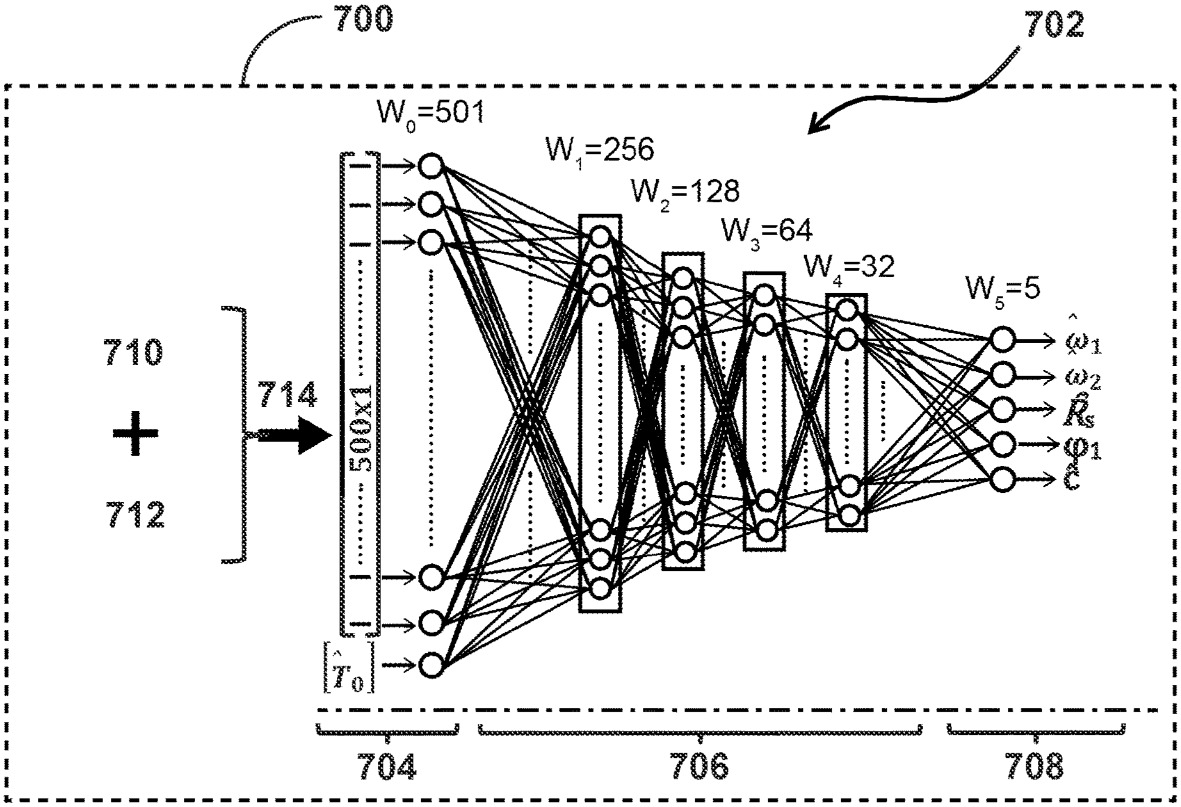
FIG. 7 illustrates a schematic of the AI model, which is configured to be used for predicting IF method outputs based on one or more carotid pressure waveforms (and/or other possible types of waveforms), in accordance with various embodiments.

FIG. 7 illustrates a schematic 700 of an AI model 702, which (as described above) is configured to be used for predicting the IF method outputs based on one or more carotid pressure waveforms (and/or other possible types of waveforms as described above). FIG. 7 shows an example schematic 700 of a trained machine learning (e.g., AI) model 702 configured (or a model ready to be trained) for predicting the IF method's outputs from a single carotid pressure waveform. In some embodiments, as shown in FIG. 7, model 702 may include an input layer 704, a plurality of hidden layers 706, an output layer 708, and/or other layers. Each of these layers (e.g., 0, 1, 2, 3, 4, and 5) may be individually weighted (W). A normalized carotid waveform 710, a dicrotic notch time 712 (normalized), and/or other information may be used as model 702 inputs 714. Model 702 outputs may comprise predicted normalized IF parameters as shown and described above.

Figure 8:
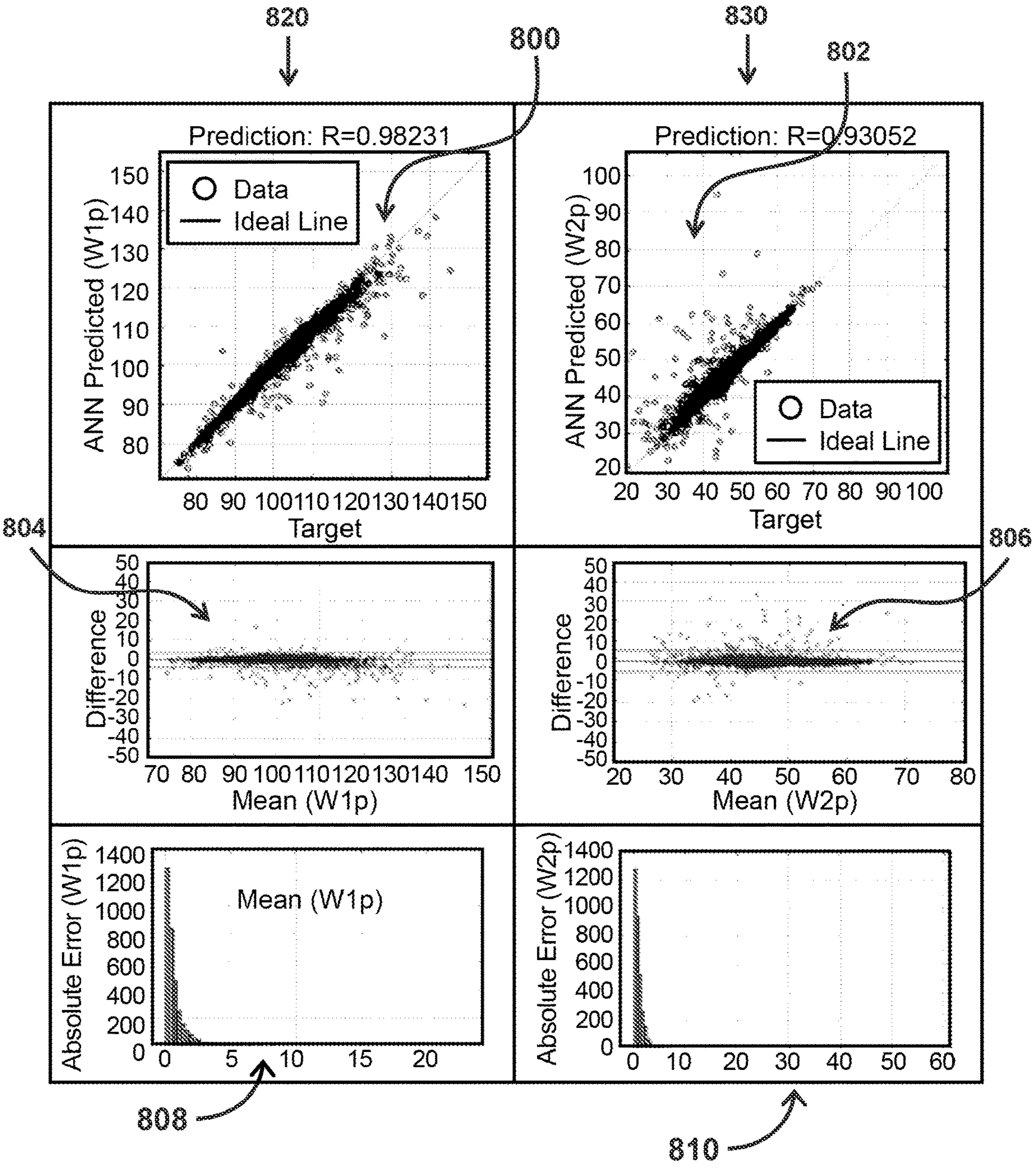
FIG. 8 illustrates evaluation plots including regression plots, Bland-Altman plots, and error histograms for first and second scaled IFs (reduced-order parameters in this use case) predicted by the AI model.

In one example use case, an AI model (e.g., model 702) was configured as described above and blindly tested on clinical data. FIG. 8 illustrates evaluation plots including regression plots 800 and 802, Bland-Altman plots 804 and 806, and error histograms 808 and 810 for first 820 and second 830 scaled intrinsic frequencies (reduced-order parameters in this use case) predicted by the AI model.

In some embodiments, systems, components, devices, sensors, or other hardware components, or other software based instructions, can be used to measure waveforms non-invasively (e.g., a smartwatch configured to measure an arterial blood pressure of a patient and generate an arterial blood pressure waveform representing the measured arterial blood pressures of the patient). This may include: 1—A Portable electronic hemodynamic sensor systems that can measure hemodynamic waveform. 2—A smartphone application and system, with or without ECG ability, that can be used to measure pulse waveforms for IF parameters and intrinsic phases, and PEP for the cardiac triangle mapping method. (Additional details regarding the CTM methodology, including clinical efficacy of the technique, is included within "Cardiac Triangle Mapping: A New Systems Approach for Noninvasive Evaluation of Left Ventricular End Diastolic Pressure," Pahlevan et al., Fluids 2019, 4, 16, the contents of which are incorporated herein by reference in their entirety.) 3—Optical sensors that can measure vessel wall motion. 4—an ECG system. 5—Tonometry devices that can measure pressure waveforms. 6—Microwave devices that can measure vessel wall motion. 7—Echo ultrasound devices that can measure vessel wall motion.

8—A pulseOx device for pulseOX waveform measurement. 9—Implanted pressure sensors in the large systemic vessels. 10—Inline and invasive radial or femoral catheters. 11—A computer system configured to automatically perform required computations from the acquired signals (e.g., as described above). Other non-invasive waveform measurement systems are contemplated.

The present application contemplates that the calculations disclosed in the embodiments herein may be performed in a number of ways, applying the same concepts taught herein, and that such calculations are equivalent to the embodiments disclosed.

Applications

Embodiments disclosed in present application may have a number of practical applications, and may provide a number of real-world technical solutions to existing technical problems. Some example applications include: semi-invasive and beat-to-beat monitoring of HF development in hospitals or clinical environments from clinically significant outputs; non-invasive and instantaneous detection of cardiovascular diseases from clinically significant outputs; semi-invasive and beat-to-beat monitoring and management of HF status in hospitals or clinical environments; discharge management of treated patients from hospitals; monitoring the compensated state of patients after discharge; evaluating and predicting effects of different preventive/curative drugs related to cardiovascular diseases; and/or other applications.

Figure 9:
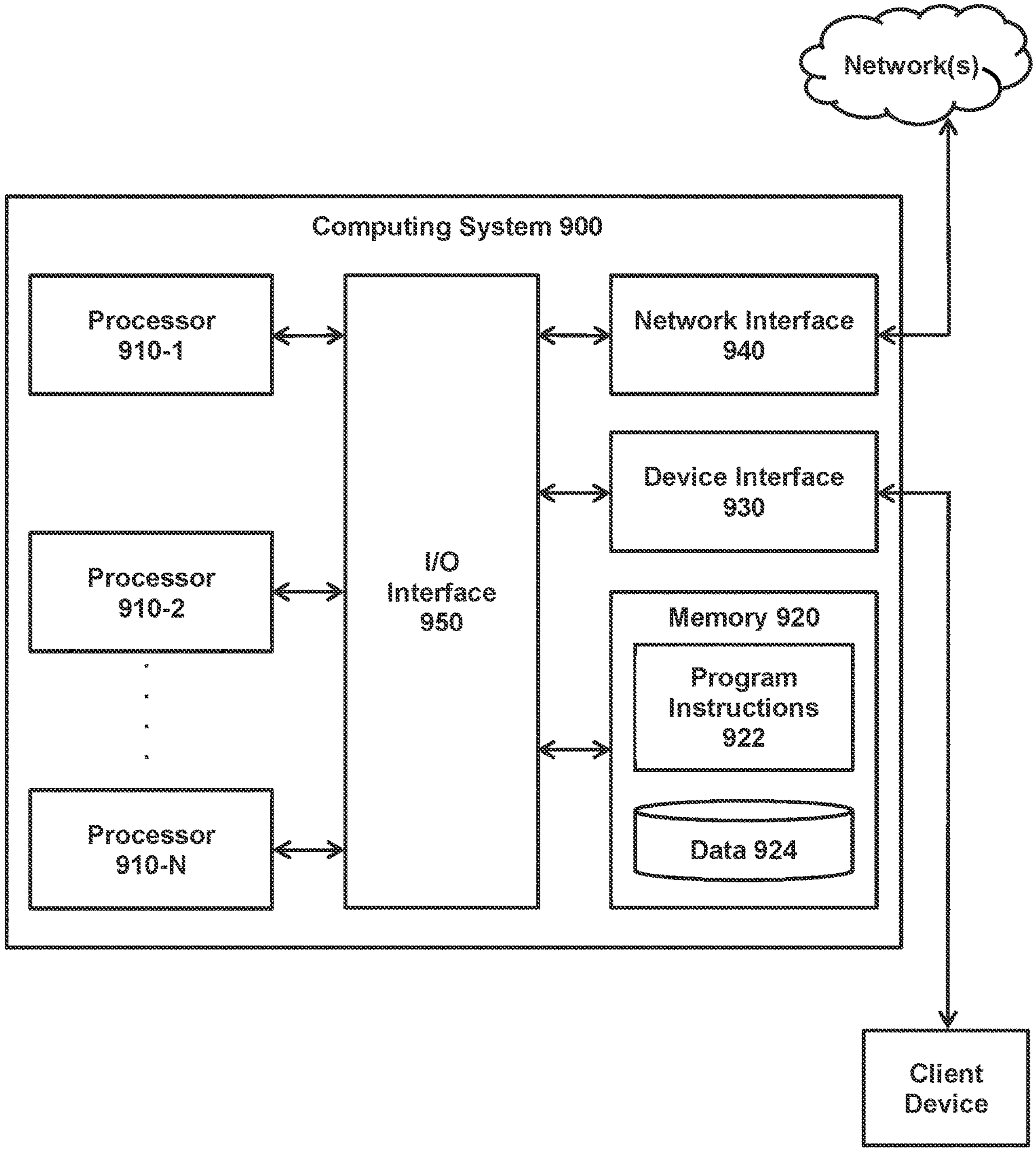
FIG. 9 is an example block diagram of a computing system upon which described program code may be executed, in accordance with various embodiments.

FIG. 9 is an example block diagram of a computing system 900 upon which described program code may be executed, in accordance with various embodiments. Various portions of systems and methods described herein, may include or be executed on one or more computer systems similar to or the same as computing system 900. Further, processes (e.g. flow 400) described herein may be executed by one or more processing systems similar to or the same as that of computing system 900.

Computing system 900 may include one or more processors (e.g., processors 910-1 to 910-N) coupled to system memory 920, an input/output I/O device interface 930, and a network interface 940 via an input/output (I/O) interface 950. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 900. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 920). Computing system 900 may be a uni-processor system including one processor (e.g., processor 910-1), or a multi-processor system including any number of suitable processors (e.g., 910-1 to 910-N). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 900 may include a plurality of computing devices (e.g., distributed computer systems) to implement various processing functions.

I/O device interface 930 may provide an interface for connection of one or more I/O devices 960 to computing system 900. I/O devices may include devices that receive input (e.g., from a user) or output information (e.g., to a user). I/O devices 960 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 960 may be connected to computing system 900 through a wired or wireless connection. I/O devices 960 may be connected to computing system 900 from a remote location. I/O devices 960 located on remote computer system, for example, may be connected to computing system 900 via a network and network interface 940. The device interface in some embodiments can be wire connected to the client device. In some other embodiments the device interface may be connected to the client device wirelessly. In some wireless embodiments, the computing system is implemented in the cloud.

Network interface 940 may include a network adapter that provides for connection of computing system 900 to a network. Network interface 940 may facilitate data exchange between computing system 900 and other devices connected to the network. Network interface 940 may support wired or wireless communication. The network may include an electronic communication network, such as the Internet, a local area network (LAN), a wide area network (WAN), a cellular communications network, or the like.

System memory 920 may be configured to store program instructions 922 or data 924. Program instructions 922 may be executable by a processor (e.g., one or more of processors 910-1 to 910-N) to implement one or more embodiments of the present techniques. Instructions 922 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 920 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 920 may include a non-transitory computer readable storage medium that may have program instructions stored thereon that are executable by a computer processor (e.g., one or more of processors 910-1-910-N) to cause the subject matter and the functional operations described herein. A memory (e.g., system memory 920) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 950 may be configured to coordinate I/O traffic between processors 910-1 to 910-N, system memory 920, network interface 940, I/O devices 960, and/or other peripheral devices. I/O interface 950 may perform protocol, timing, or other data transformations to convert data signals from one component (e.g., system memory 920) into a format suitable for use by another component (e.g., processors 910-1 to 910-N). I/O interface 950 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing system 900 or multiple computing systems 900 configured to host different portions or instances of embodiments. Multiple computing systems 900 may provide for parallel or sequential processing/execution of one or more portions of the techniques described herein.

Those skilled in the art will appreciate that computing system 900 is merely illustrative and is not intended to limit the scope of the techniques described herein. Computing system 900 may include any combination of devices or software that may perform or otherwise provide for the performance of the techniques described herein. For example, computing system 900 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computing system 900 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computing system 900 may be transmitted to computing system 900 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

The present techniques will be better understood with reference to the following enumerated embodiments:

1. A method, comprising: receiving patient data having one or more cardiovascular waveforms related to a cardiac cycle or a vasculature of a patient; calculating, from the one or more waveforms, at least one output from a signal analysis method; inputting, into a trained machine learning model, the one or more cardiovascular waveforms; determining, utilizing the trained model, clinically relevant parameters from the signal analysis method (e.g., IF method); and in response to determining the at least one output, providing information about an underlying pathology to a user.

2. The method of embodiment 1, wherein the cardiovascular waveforms comprise at least one of: arterial blood pressure waveforms, vessel displacement waveforms, pulse-ox waveforms, or electrocardiograms (ECGs).

3. The method of any of the previous embodiments, wherein the trained machine learning model comprises a trained artificial intelligence model.

4. The method of any of the previous embodiments, wherein the trained artificial intelligence model is a feed-forward neural network model.

5. The method of any of the previous embodiments, wherein the one or more waveforms are generated based on one or more pulse pressure measurements, one or more pulse measurements, one or more blood pressure measurements, or one or more pulse oximeter measurements.

6. The method of any of the previous embodiments, further comprising: calculating, from the one or more waveforms, a first intrinsic frequency and a first intrinsic phase associated with the cardiac cycle of the patient; and calculating, from the one or more waveforms, a second intrinsic frequency and a second intrinsic phase associated with the vasculature, wherein the parameters comprise the first intrinsic frequency, the first intrinsic phase, the second intrinsic frequency, and the second intrinsic phase.

7. The method of any of the previous embodiments, wherein the first intrinsic phase comprises a first intrinsic phase angle and the second intrinsic phase comprises a second intrinsic phase angle.

8. The method of any of the previous embodiments, further comprising: calculating, from the one or more waveforms, a diastolic intrinsic envelope, a systolic intrinsic envelope, and a relative height of the dicrotic notch (RHDN), and wherein the calculating of the first intrinsic frequency, the first intrinsic phase, the second intrinsic frequency, and the second intrinsic phase comprises minimization of a function of the calculated frequencies, phases, and envelopes.

9. The method of any of the previous embodiments, further comprising: training an initial machine learning model to obtain the trained machine learning model, wherein the trained machine learning model is trained to compute clinical (physiological) indices (parameters) by at least: inputting training data comprising first intrinsic phase training data, wherein the training data is from a subject that had a specific cardiovascular disease prior to collecting of the training data.

10. The method of any of the previous embodiments, further comprising steps for training a machine learning model to obtain the trained machine learning model.

11. The method of any of the previous embodiments, further comprising: obtaining a pulse pressure waveform measurement, wherein calculating signal analysis parameters are based on the pulse pressure waveform measurement which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, or a pulse-ox waveform.

12. The method of any of the previous embodiments, wherein the calculating of signal (waveform) analysis parameters is based on a measurement of blood flow.

13. The method of any of the previous embodiments, wherein a client device having a diagnosis module that includes the trained model and performs a determination of a specific cardiovascular disease is provided.

14. The method of any of the previous embodiments, wherein the client device is a smartphone.

15. The method of any of the previous embodiments, wherein the client device is a wearable device.

16. The method of any of the previous embodiments, wherein the client device is operatively coupled to at least one of a wearable device or another client device to capture a pressure waveform.

17. The method of any of the previous embodiments, further comprising: calculating, from the one or more waveforms, a Fourier transform harmonic information (truncated by any frequency number) of any cardiovascular waveform.

18. The method of any of the previous embodiments, further comprising: calculating, from the one or more waveforms, any basis function expansion extracted from any cardiovascular waveform.

19. The method of any of the previous embodiments, wherein the basis function expansion comprises an eigenfunction expansion.

20. A method, comprising: receiving patient data having one or more waveforms related to a cardiac cycle or a vasculature of a patient; calculating, from the one or more waveforms, at least one clinically relevant parameter from any signal (waveform) analysis method; inputting, into a trained machine learning model, one or more cardiovascular waveforms; determining, utilizing the trained model, a physiological parameter; and in response to determining the physiological parameter, providing an indication of cardiac risk to a user.

21. The method of any of the previous embodiments, wherein cardiovascular waveforms comprise at least one of: arterial blood pressure waveforms, vessel displacement waveforms, pulse-ox waveforms, or electrocardiograms (ECGs).

22. The method of any of the previous embodiments, wherein the trained model comprises a trained artificial intelligence (AI) model.

24. The method of any of the previous embodiments, wherein the trained artificial intelligence model is a feed-forward neural network model.

25. The method of any of the previous embodiments, wherein the one or more waveforms are generated based on one or more pulse pressure measurements, one or more pulse measurements, one or more blood pressure measurements, or one or more pulse oximeter measurements.

26. The method of any of the previous embodiments, further comprising: calculating, from the one or more waveforms, a first intrinsic frequency and a first intrinsic phase associated with a cardiac cycle; and calculating, from the one or more waveforms, a second intrinsic frequency and a second intrinsic phase associated with vasculature, wherein myocardial parameters comprise the first intrinsic frequency, the first intrinsic phase, the second intrinsic frequency, and the second intrinsic phase.

27. The method of any of the previous embodiments, further comprising: calculating, from the one or more waveforms, a diastolic intrinsic envelope, and a systolic intrinsic envelope, and wherein the calculating of the first intrinsic frequency, the first intrinsic phase, the second intrinsic frequency, and the second intrinsic phase comprises minimization of a function of the calculated frequencies, phases, and envelopes.

28. The method of any of the previous embodiments, further comprising: training the trained model to directly detect signal analysis outputs or clinical or physiological indices by at least: inputting training data comprising first intrinsic phase training data, wherein the training data is from a patient with a specific cardiovascular disease (target for diagnosis).

29. The method of any of the previous embodiments, further comprising steps for training a machine learning model to obtain the trained machine learning model.

30. The method of any of the previous embodiments, further comprising: obtaining a pulse pressure waveform measurement, wherein calculating clinical or physiological parameters are based on the pulse pressure waveform measurement which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, pulmonary vessel wall waveform, pulmonary pressure waveform, or a pulse-ox waveform.

31. The method of any of the previous embodiments, wherein calculating clinical or physiological parameters (or signal analysis outputs) is based on a measurement of blood flow.

32. The method of any of the previous embodiments, wherein a client device having a diagnosis module that includes the trained model performs a determination of an occurrence for any cardiovascular disease.

33. The method of any of the previous embodiments, wherein the client device is a smartphone.

34. The method of any of the previous embodiments, wherein the client device is a wearable device.

35. The method of any of the previous embodiments, wherein the client device is operatively coupled to at least one of a wearable device or another client device to capture a pressure waveform.

36. A client device comprising: one or more processors configured to execute computer program instructions to effectuate the method of any of the previous embodiments.

37. A system comprising: memory storing computer program instructions; and one or more processors configured to execute the computer program instructions to effectuate the method of any of the previous embodiments.

38. A wearable device comprising: one or more processors configured to execute computer program instructions to effectuate the method of any of the previous embodiments.

39. A non-transitory computer-readable medium storing computer program instructions that, when executed by one or more processors, effectuate operations comprising the method of any of the previous embodiments.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g., within a data center or geographically), or otherwise differently organized. The functionality described herein may be provided by one or more processors of one or more computers executing code stored on a tangible, non-transitory, machine-readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several inventions. Rather than separating those inventions into multiple isolated patent applications, applicants have grouped these inventions into a single document because their related subject matter lends itself to economies in the application process. But the distinct advantages and aspects of such inventions should not be conflated. In some cases, embodiments address all of the deficiencies noted herein, but it should be understood that the inventions are independently useful, and some embodiments address only a subset of such problems or offer other, unmentioned benefits that will be apparent to those of skill in the art reviewing the present disclosure. Due to costs constraints, some inventions disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such inventions or all aspects of such inventions.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

In this text, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A system comprising:

at least one programmable processor; and a non-transitory machine-readable medium storing instructions which, when executed by the at least one programmable processor, cause the at least one programmable processor to perform operations comprising:

receiving patient data having one or more cardiovascular waveforms related to a cardiac cycle of a vasculature of a patient;

calculating, from the one or more cardiovascular waveforms, at least one output from a signal analysis method;

inputting, into a trained artificial intelligence (AI) model, the one or more cardiovascular waveforms;

determining, utilizing the trained AI model, clinically relevant output parameters for the signal analysis method;

calculating, from the one or more cardiovascular waveforms, a first intrinsic frequency and a first intrinsic phase associated with the cardiac cycle;

calculating, from the one or more cardiovascular waveforms, a second intrinsic frequency and a second intrinsic phase associated with the vasculature;

wherein the clinically relevant output parameters comprise the first intrinsic frequency, the first intrinsic phase, the second intrinsic frequency, and the second intrinsic phase;

training the trained AI model to compute the clinically relevant output parameters by at least:

inputting training data comprising first intrinsic phase training data, wherein the training data is from a subject that had a specific cardiovascular disease prior to collecting of the training data; and in response to determining the clinically relevant output parameters, providing information about an underlying pathology to a user.

2. The system of claim 1, wherein the one or more cardiovascular waveforms are from a pulse pressure measurement or a pulse oximeter measurement.

3. The system of claim 1, the operations further comprising:

calculating, from the one or more cardiovascular waveforms, a diastolic intrinsic envelope, and a systolic intrinsic envelope, and relative height of a dicrotic notch (RHDN), and wherein the calculating of the first intrinsic frequency, the first intrinsic phase, the second intrinsic frequency, and the second intrinsic phase comprises minimization of a function of the calculated frequencies, phases, and envelopes.

4. The system of claim 1, the operations further comprising:

obtaining a pulse pressure waveform measurement, wherein the calculating of the at least one output from the signal analysis method is based on the pulse pressure waveform measurement which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, or a pulse-ox waveform.

5. The system of claim 1, wherein the calculating of the at least one output from the signal analysis method is based on a measurement of blood flow.

6. The system of claim 1, further comprising a client device having a diagnosis module that includes the trained AI model and provides the information about the underlying pathology to a user as a determination of a specific cardiovascular disease.

7. The system of claim 6, wherein the client device is a smartphone or a wearable device.

8. The system of claim 1, the operations further comprising:

calculating, from the one or more cardiovascular waveforms, Fourier transform harmonic information truncated by any number of frequency of any cardiovascular waveform.

9. The system of claim 1, the operations further comprising:

calculating, from the one or more cardiovascular waveforms, a basis function expansion extracted from a cardiovascular waveform.

10. A non-transitory, machine-readable medium storing instructions which, when executed by at least one programmable processor, cause the at least one programmable processor to perform operations comprising:

receiving patient data having one or more cardiovascular waveforms related to a cardiac cycle or a vasculature of a patient;

calculating, from the one or more cardiovascular waveforms, at least one output from a signal analysis method;

inputting, into a trained artificial intelligence (AI) model, the one or more cardiovascular waveforms, the AI model comprising a neural network;

determining, utilizing the trained AI model, clinically relevant output parameters for the signal analysis method, the clinically relevant output parameters comprising a physiological parameter;

calculating, from the one or more cardiovascular waveforms, a first intrinsic frequency and a first intrinsic phase associated with the cardiac cycle;

calculating, from the one or more cardiovascular waveforms, a second intrinsic frequency and a second intrinsic phase associated with the vasculature, wherein the physiological parameter comprises myocardial parameters, and the myocardial parameters comprise the first intrinsic frequency, the first intrinsic phase, the second intrinsic frequency, and the second intrinsic phase;

training the neural network to detect the clinically relevant output parameters for the signal analysis method, including signal analysis outputs or clinical or physiological indices, directly by at least:

inputting training data comprising first intrinsic phase training data, wherein the training data is from a patient with a specific cardiovascular disease which is a target for diagnosis; and in response to determining the physiological parameter, providing an indication of a cardiac risk to the patient.

11. The medium of claim 10, wherein the one or more cardiovascular waveforms are from a pulse pressure measurement or a pulse oximeter measurement.

12. The medium of claim 10, the operations further comprising:

calculating, from the one or more cardiovascular waveforms, a diastolic intrinsic envelope, and a systolic intrinsic envelope, wherein the calculating of the first intrinsic frequency, the first intrinsic phase, the second intrinsic frequency, and the second intrinsic phase comprises minimization of a function of calculated frequencies, phases, and envelopes.

13. The medium of claim 10, the operations further comprising:

obtaining a pulse pressure waveform measurement, wherein the calculating of the clinically relevant or physiological parameters are based on the pulse pressure waveform measurement, which is one or more of a carotid pressure waveform, an aortic wall waveform, a carotid vessel wall waveform, a radial pressure waveform, a radial vessel wall waveform, a brachial pressure waveform, a brachial vessel wall waveform, a femoral pressure waveform, a femoral vessel wall waveform, pulmonary vessel wall waveform, pulmonary pressure waveform, or a pulse-ox waveform.

14. The medium of claim 10, wherein the calculating of the clinically relevant or physiological parameters is based on a measurement of blood flow.

15. The medium of claim 10, wherein the medium and the processor reside on a client device having a diagnosis module that includes the trained AI model and provides the indication of the cardiac risk to the patient for a cardiovascular disease.

16. The medium of claim 15, wherein the client device is a smartphone or a wearable device.

* * * * *